(12) United States Patent
Ugawa et al.

(10) Patent No.: US 10,882,043 B2
(45) Date of Patent: Jan. 5, 2021

(54) URINE SAMPLING CONTAINER

(71) Applicant: Atleta Co., Ltd., Osaka (JP)

(72) Inventors: Hiroaki Ugawa, Osaka (JP); Ichiro Morimoto, Hyogo (JP); Satoshi Miyatake, Osaka (JP)

(73) Assignee: Atleta Co., Ltd., Osaka (JP)

( * ) Notice: Subject to any disclaimer, the term of this patent is extended or adjusted under 35 U.S.C. 154(b) by 226 days.

(21) Appl. No.: 15/770,259

(22) PCT Filed: Apr. 28, 2016

(86) PCT No.: PCT/JP2016/002232
§ 371 (c)(1),
(2) Date: Apr. 23, 2018

(87) PCT Pub. No.: WO2017/072983
PCT Pub. Date: May 4, 2017

(65) Prior Publication Data
US 2018/0311667 A1 Nov. 1, 2018

(30) Foreign Application Priority Data

Oct. 26, 2015 (JP) .................................. 2015-210139

(51) Int. Cl.
| | | |
|---|---|---|
| *B01L 1/00* | (2006.01) | |
| *B01L 3/00* | (2006.01) | |
| *G01N 1/10* | (2006.01) | |
| *A61B 10/00* | (2006.01) | |
| *G01N 33/48* | (2006.01) | |

(52) U.S. Cl.
CPC ........ *B01L 3/50825* (2013.01); *A61B 10/007* (2013.01); *G01N 1/10* (2013.01); *G01N 33/48* (2013.01); *B01L 2300/0832* (2013.01)

(58) Field of Classification Search
CPC ....................................................... G01N 1/00
See application file for complete search history.

(56) References Cited

U.S. PATENT DOCUMENTS

2012/0183453 A1* 7/2012 Boehm ................ B01L 3/0206
422/501

FOREIGN PATENT DOCUMENTS

| EP | 0296799 A1 | 12/1988 |
| EP | 1063508 A1 | 12/2000 |
| JP | 2004-219278 A | 8/2004 |

(Continued)

OTHER PUBLICATIONS

Extended European Search Report dated Oct. 17, 2018 for corresponding EP Application No. 16859224.4.

(Continued)

*Primary Examiner* — Jyoti Nagpaul
(74) *Attorney, Agent, or Firm* — Renner, Otto, Boisselle & Skalr, LLP

(57) ABSTRACT

In a urine sampling container 1, a retaining mechanism 15 is provided on opening end sides of a urine collection tube 3 and a cover tube 4 to prevent the cover tube 4 from being removed from the urine collection tube 3 in a state in which the urine collection tube 3 is inserted to and fitted in the cover tube 4, so as to keep the urine collection tube 3 and a storage tube 2 securely coupled with each other at the time of urine collection and to allow the storage tube 2 to be easily removed from the urine collection tube 3 at the time of examination.

10 Claims, 15 Drawing Sheets

(56) References Cited

FOREIGN PATENT DOCUMENTS

| JP | 2009-047537 A | | 3/2009 |
|---|---|---|---|
| JP | 2013-40788 | * | 2/2013 |
| JP | 2013-040788 A | | 2/2013 |
| JP | 2015-049202 A | | 3/2015 |
| WO | 99/032871 A1 | | 7/1999 |

OTHER PUBLICATIONS

International Search Report for corresponding App. No. PCT/JP2016/002232, dated Jul. 19, 2016.

* cited by examiner

URINE SAMPLING CONTAINER

TECHNICAL FIELD

The present invention relates to a urine sampling container used for urinalysis performed in a hospital, a test center or the like.

BACKGROUND ART

In general, a large number of urinalysis are conducted at hospitals, test centers, or the like.

As disclosed in Patent Document 1, a typical urine sampling container used for that urinalysis includes a storage tube storing urine, a urine collection tube attached on an opening end of the storage tube and including a side surface having a urine collection port, and a cover tube covering the urine collection port so that the urine collection tube can be inserted freely.

The urine sampling container is in an assembled state in which the urine collection tube is attached to the storage tube. Then, the examinee grips the storage tube with the urine collection tube oriented downward. When the examinee applies urine to the urine collection port, the urine accumulates in the storage tube. Then, the collection of urine is completed.

Next, the urine collection tube oriented downward is inserted into the cover tube. As a result, the urine collection tube, which is a dirty part, is covered. Then, the urine sampling container is, for example, inverted upside down and transferred to the laboratory or the like while the storage tube oriented downward is inserted in the container stand or the like.

CITATION LIST

Patent Document

Patent Document 1: Japanese Unexamined Patent Publication No. 2013-040788

SUMMARY OF THE INVENTION

Technical Problem

In the typical urine sampling container, the storage tube and the urine collection tube are configured to be screwed together. Specifically, a male screw formed on an outer peripheral surface of the opening side end of the storage tube and a female screw formed on an inner peripheral surface of the opening side end of the urine collection tube are screwed so that the storage tube and the urine collection tube are integrated to collect urine.

As such, in the typical urine sampling container, the storage tube and the urine collection tube are screwed together, and thus, at the time of urine collection, the urine collection tube is unlikely to be removed from the storage tube by accident. On the other hand, in the typical urine sampling container, the storage tube and the urine collection tube are screwed together. Thus, at the time of examination after urine collection, it is necessary to loosen the male thread of the storage tube with respect to the female thread of the urine collection tube to remove the storage tube from the urine collection tube. Thus, the operation at the examination was complicated. In contrast, if the storage tube is easily removed from the urine collection tube at the time of examination, it is conversely difficult to firmly join the urine collection tube and the storage tube at the time of urine collection. In other words, in the typical urine sampling container, it is difficult to firmly join the urine collection tube and the storage tube at the time of urine collection whereas to easily remove the storage tube from the urine collection tube at the time of examination.

In view of the foregoing, it is an object of the present invention to provide a urine sampling container having a storage tube, a urine collection tube, and a cover tube, wherein the urine collection tube and the storage tube are to securely joined at the time of urine collection and the storage tube is easily removed from the urine collection tube at the time of examination.

SUMMARY OF THE INVENTION

In a first aspect of the present disclosure, a urine sampling container includes a storage tube formed as an elongated tube and storing urine, where one end of the storage tube is a closed end and the other end of the storage tube is an opening end; a urine collection tube formed as an elongated tube and including a side surface having a urine collection port, where one end of the urine collection tube is a closed end and the other end of the urine collection tube is an opening end freely attachable to and detachable from the opening end of the storage tube; and a cover tube formed as an elongated tube, formed so that the urine collection tube can be inserted to and removed from the cover tube, and covering the urine collection port, where one end of the cover tube is a closed end and the other end of the cover tube is an opening end.

The urine sampling container includes a retaining mechanism provided near the opening ends of the urine collection tube and the cover tube to prevent the cover tube from being removed from the urine collection tube in a state in which the urine collection tube is inserted and fitted in the cover tube.

In this first aspect, at the time of urine collection, the cover tube is not attached on the urine sampling container, and the storage tube and the urine collection tube are joined. At this time, the difference in the wall thickness between the storage tube and the urine collection tube is small (or there is no difference in the wall thickness), and thus the difference in the rigidity between the storage tube and the urine collection tube is small, such that the portion coupled by the storage tube and the urine collection tube is less likely to be deformed. On the other hand, when the cover tube is attached to the urine collection tube after the urine collection, the retaining mechanism integrates the opening ends of the urine collection tube and the cover tube. Thus, the rigidity of the integrated portion between the urine collection tube and the cover tube is larger than that of the storage tube, and the storage tube is easily deformed with respect to the urine collection tube and the cover tube.

In a second aspect according to the first aspect of the present disclosure, the retaining mechanism includes a flange section formed on the urine collection tube, and a stopper tube formed on the cover tube allowing an insertion of the flange section of the urine collection tube, and on an inner peripheral surface of the stopper tube, a stopper protrusion to be engaged with the flange section is formed.

In this second aspect, the cover tube is not removed from the urine collection tube by inserting the flange section into the stopper tube and engaging the flange section with the stopper protrusion.

In a third aspect according to the second aspect of the present disclosure, an inner peripheral surface of the stopper protrusion is formed as an inclined surface of which the amount of protrusion increases from the opening end of the stopper tube toward the back thereof.

In this third aspect, when the flange section is inserted into the stopper tube, the flange section passes over the inclined surface and engages with the stopper protrusion, so that the cover tube is not removed from the urine collection tube.

In a fourth aspect according to the third aspect of the present disclosure, the stopper tube has a slit positioned radially outward of the flange section.

In this fourth aspect, when the flange section is inserted into the stopper tube and engages with the stopper protrusion, the flange section is positioned in the slit.

In a fifth aspect according to the first aspect of the present disclosure, the urine collection tube and the cover tube are configured to be screwed together, the retaining mechanism includes a first stopper raised section formed on the urine collection tube, and a second stopper raised section formed on the cover tube, and the first stopper raised section and the second stopper raised section are configured to prohibit a rotation in a direction of loosening a screw in a state in which the urine collection tube is screwed into the cover tube.

In this fifth aspect, when the urine collection tube is screwed to the cover tube, the first stopper raised section and the second stopper raised section are engaged and prohibited from turning in the reverse direction, and the cover tube is not removed from the urine collection tube.

In a sixth aspect according to any one of the first to fifth aspects of the present disclosure, a holding mechanism for keeping the storage tube inserted in the urine collection tube is formed on an outer peripheral surface of the storage tube and an inner peripheral surface of the urine collection tube, at a position displaced from a joint section at which the urine collection tube and the cover tube overlap to be integrated together, and the holding mechanism includes a circumferential raised section formed on the outer peripheral surface of the storage tube, and a circumferential recessed section formed on the inner peripheral surface of the urine collection tube and fitted with the circumferential raised section.

In this sixth aspect, when the circumferential raised section formed on the outer peripheral surface of the storage tube and the circumferential recessed section formed on the inner peripheral surface of the urine collection tube are fitted with each other, the storage tube is kept inserted in the urine collection tube.

In a seventh aspect according to the sixth aspect of the present disclosure, the circumferential raised section of the holding mechanism includes a first circumferential raised section located closer to the opening end of the storage tube, and a second circumferential raised section located closer to the closed end than the first circumferential raised section, and the circumferential recessed section of the holding mechanism includes a first shoulder coming into contact with the first circumferential raised section from the opening end of the storage tube, and a second shoulder coming into contact with the second circumferential raised section from the closed end of the storage tube.

In this seventh aspect, when the circumferential raised section formed on the outer peripheral surface of the storage tube and the circumferential recessed section formed on the inner peripheral surface of the urine collection tube are fitted with each other, the first shoulder comes into contact with the first circumferential raised section from the opening end of the storage tube, and the second shoulder comes into contact with the second circumferential raised section from the closed end of the storage tube. Then, the storage tube is kept inserted in the urine collection tube.

In an eighth aspect according to any one of the first to seventh aspects of the present disclosure, the urine collection tube is made of a discoloration material exhibiting a respective different color at a first temperature corresponding to a human body temperature and at a second temperature lower than the first temperature.

In this eighth aspect, when urine is applied to the urine collection tube at the time of urine collection, the urine collection tube is discolored due to the influence of a urine temperature which is substantially corresponding to the human body temperature. In some conventional cases, it was difficult to determine a completion of urine collection in an environment such as dark surroundings. In this eighth aspect, the urine collection tube is discolored so that the examinee can recognize a completion of urine collection.

In a ninth aspect according to the eighth aspect of the present disclosure, the urine collection tube is made of a material that is in a non-coloring state at the second temperature and changes from the non-coloring state to a coloring state when the temperature changes from the second temperature to the first temperature at the time of urine collection.

In this ninth aspect, when urine is applied to the urine collection tube at the time of urine collection, the urine collection tube is discolored from the non-coloring state to the coloring state due to the influence of a urine temperature. In some conventional cases, it was difficult to determine a completion of urine collection in an environment such as dark surroundings. In this ninth aspect, the urine collection tube is changed to the coloring state so that the examinee can recognize a completion of urine collection.

In a tenth aspect according to the eighth aspect of the present disclosure, the urine collection tube is made of a material that is in a coloring state at the second temperature and changes from the coloring state to a non-coloring state when the temperature changes from the second temperature to the first temperature at the time of urine collection.

In this tenth aspect, when urine is applied to the urine collection tube at the time of urine collection, the urine collection tube having had a lower temperature is discolored from the coloring state to the non-coloring state due to the influence of a urine temperature. In some conventional cases, it was difficult to determine a completion of urine collection in an environment such as dark surroundings. In this tenth aspect, the urine collection tube is changed to the non-coloring state so that the examinee can recognize a completion of urine collection.

Advantages of the Invention

According to the first aspect of the present disclosure, at the time of urine collection, the difference in the rigidity between the storage tube and the urine collection tube is small, and the coupling portion between the storage tube and the urine collection tube is less likely to be deformed. Thus, the storage tube and the urine collection tube are reliably joined and not easily disengaged. On the other hand, at the time of examination, the rigidity of the urine collection tube and the cover tube integrated together is larger than that of the storage tube, and the storage tube is easily deformed at the coupling portion between the urine collection tube and the cover tube. Thus, the examiner can easily bend and disengage the storage tube into the "L" shape at the coupling portion with respect to the urine collection tube and the cover tube integrated together. As such, the first aspect of the present disclosure provides the configuration in which the urine collection tube and the storage tube are securely coupled at the time of urine collection, and the storage tube is easily disengaged from the urine collection tube at the time of examination.

According to the second to fourth aspects of the present disclosure, the cover tube is not removed from the urine collection tube by inserting the flange section into the stopper tube and engaging the flange section with the stopper protrusion. Thus, the retaining mechanism can be achieved with a simple configuration.

According to the fifth aspect of the present disclosure, when the urine collection tube is screwed to the cover tube, the first stopper raised section and the second stopper raised section are engaged and prohibited from turning in the reverse direction, and the cover tube is not removed from the urine collection tube. Thus, the retaining mechanism can be achieved with a simple configuration.

According to the sixth aspect of the present disclosure, when the circumferential raised section formed on the outer peripheral surface of the storage tube and the circumferential recessed section formed on the inner peripheral surface of the urine collection tube are fitted with each other, the storage tube is kept inserted in the urine collection tube. Thus, without a screw junction or the like, the retaining mechanism can be achieved with a simple configuration.

According to the seventh aspect of the present disclosure, when the circumferential raised section formed on the outer peripheral surface of the storage tube and the circumferential recessed section formed on the inner peripheral surface of the urine collection tube are fitted with each other, the first shoulder comes into contact with the first circumferential raised section, located closer to the opening end of the storage tube, from the opening end of the storage tube, and the second shoulder comes into contact with the second circumferential raised section, located closer to the closed end than the first circumferential raised section from the closed end of the storage tube. Then, the storage tube is kept inserted in the urine collection tube. The set of the first circumferential raised section and the first shoulder is located closer to the opening end of the storage tube, and the set of the second circumferential raised section and the second shoulder is located closer to the closed end of the storage tube so that these set are located apart from each other. Thus, the storage tube is inserted in and stably held in the urine collection tube.

According to the eighth to tenth aspects of the present disclosure, when urine is applied to the urine collection tube at the time of urine collection, the urine collection tube having had a low temperature is discolored due to the influence of a urine temperature (approximately a body temperature). In some conventional cases, it was difficult to determine a completion of urine collection in an environment such as dark surroundings. In these eighth to tenth aspect, the urine collection tube is discolored so that the examinee can surely recognize a completion of urine collection.

DESCRIPTION OF EMBODIMENTS

Embodiments of the present invention will be described in detail below with reference to the drawings.

First Embodiment of the Invention

The first embodiment of the present invention will be described.

Figure 1:
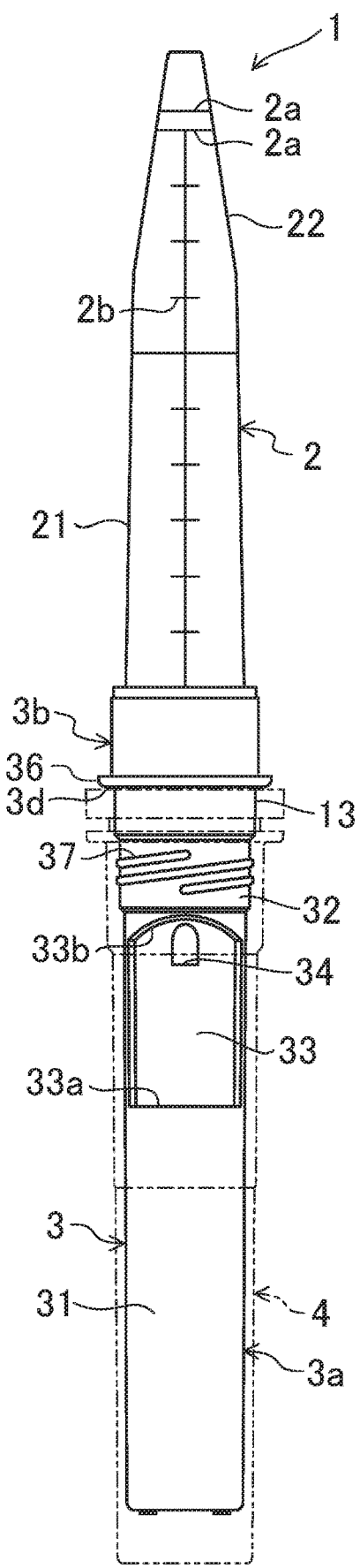
FIG. 1 is a front view of a urine sampling container according to a first embodiment of the present invention, a cover tube being indicated by virtual lines.
Figure 2:
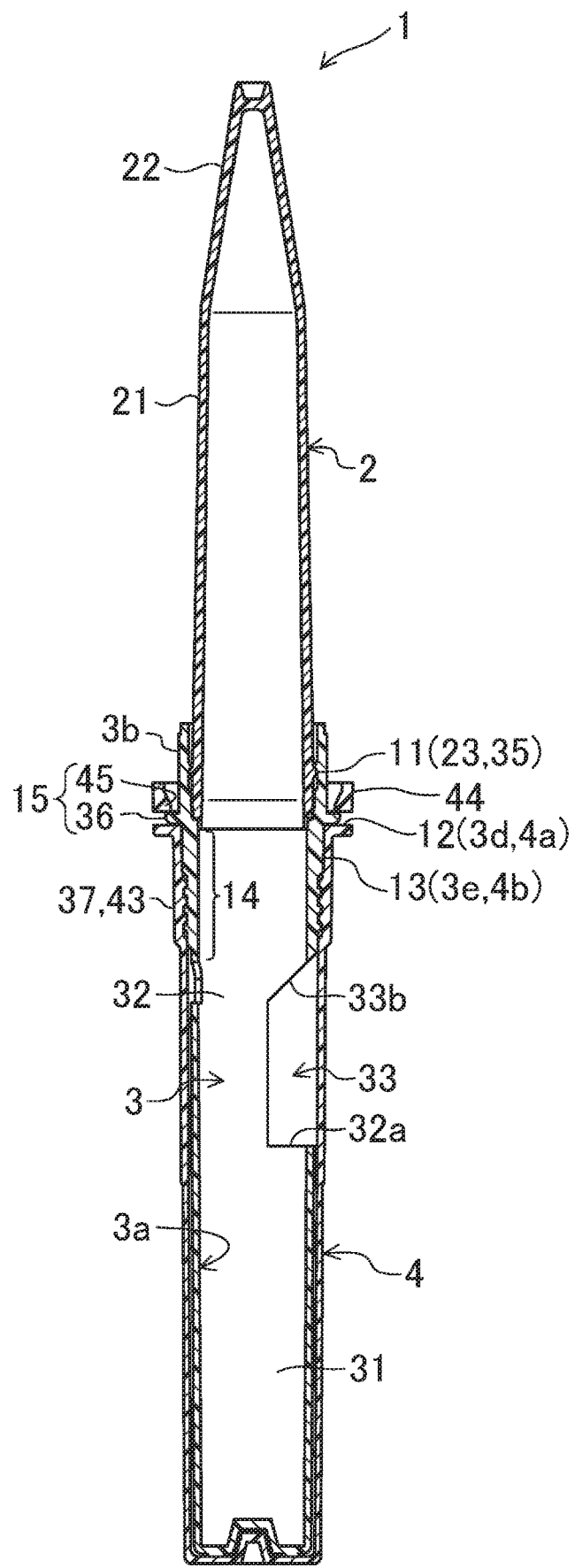
FIG. 2 is a longitudinal sectional view of the urine sampling container with the cover tube.

A urine sampling container 1 illustrated in FIGS. 1 and 2 is a container for collecting urine at the time of a urinalysis conducted at a hospital or the like.

The urine sampling container 1 includes a storage tube 2 for storing collected urine, a urine collection tube 3 for urine collection and measurement, and a cover tube 4 detachably attached to the urine collection tube 3.

Figure 3:
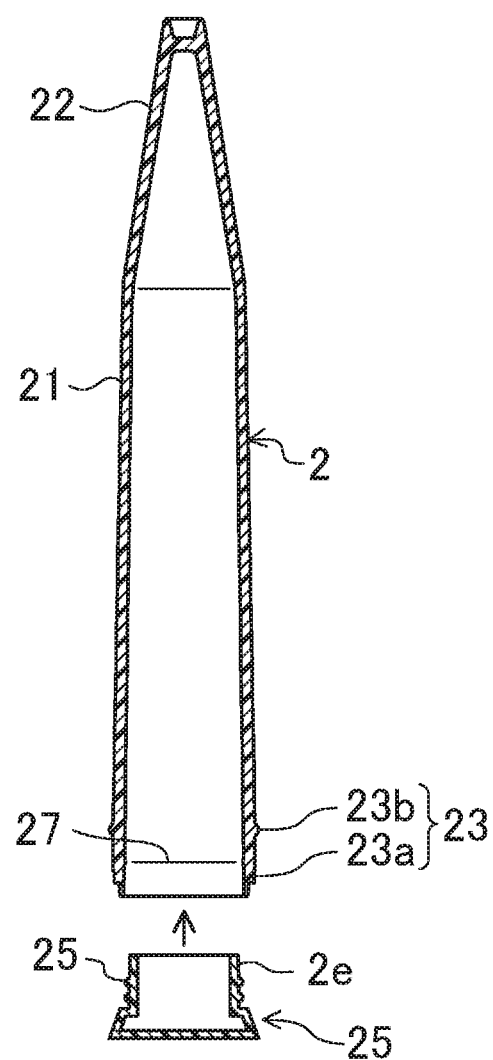
FIG. 3 is a longitudinal sectional view of a storage tube.

As illustrated in FIG. 3, the storage tube 2 is formed as an elongated tubular body where one end thereof is closed and the other end is opened. The storage tube 2 is formed from a transparent material such as a synthetic resin. Note that the material of the storage tube 2 is not limited to a transparent material, and may be formed from various materials such as a colored translucent material.

The storage tube 2 includes a main body 21, occupying substantially a half of the entirety, in the lower side of FIG. 3, and a tapered section 22, occupying substantially a half of the entirety, in the upper side of FIG. 3. The storage tube 2 is configured as a Spitz tube having an outer diameter and a length applicable to a urinalysis device.

The main body 21 of the storage tube 2 is formed in a tapered shape slightly thinner toward the tapered section 22, and includes an opening end having an outer peripheral surface having a circumferential raised section 23 constituting a holding mechanism 11 for keeping the storage tube 2 attached to the urine collection tube 3. The circumferential raised section 23 includes a first circumferential raised section 23a and a second circumferential raised section 23b. The tapered section 22 of the storage tube 2 is continuous with the main body 21 and formed in a tapered shape narrower toward the closed end. The tapered section 22 of the storage tube 2 has a larger taper angle than the main body 21.

The tapered section 22 of the storage tube 2 includes a tip end having a first marked line 2a and a second marked line 2a. The first marked line 2a and the second marked line 2a indicates the amount of residual urine; are used to centrifuge collected urine, discard a supernatant, and collect a sample for a urine sediment test (15 µl; microliter); and are set to display the storage amounts of 0.1 ml (milliliter) and 0.2 ml (milliliter), respectively.

The storage tube 2 is labeled with urine collection scales 2b indicating the urine collection amount. The urine collection scales 2b are attached in the longitudinal direction of the storage tube 2 so that the urine collection amount can be specified.

Note that the urine sampling container 1 includes a cap 25 for the storage tube 2. The cap 25 is fitted into the main body 21 of the storage tube 2 and completely closes the storage tube 2.

Figure 4:
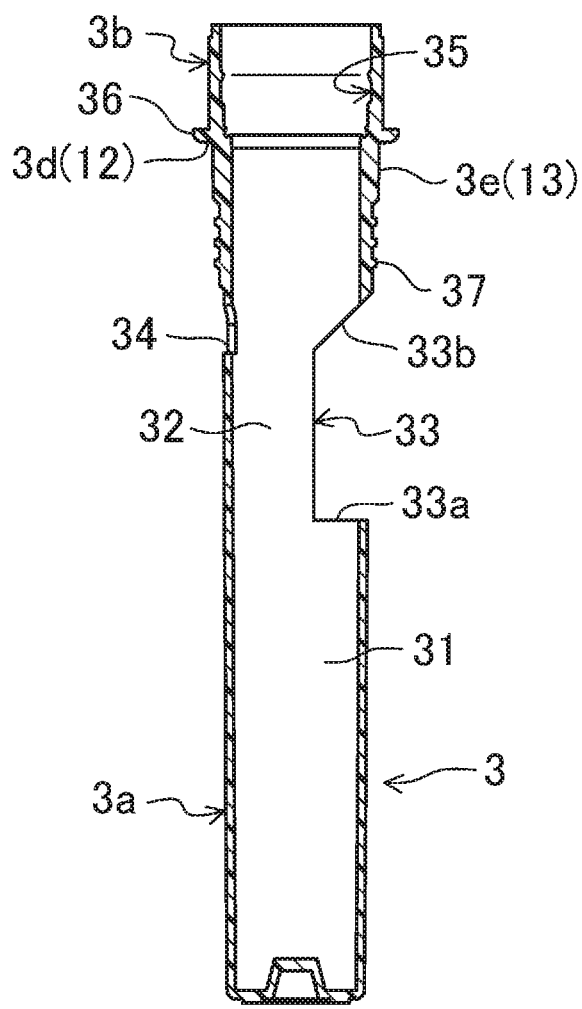
FIG. 4 is a longitudinal sectional view of a urine collection tube.

As illustrated in FIG. 4, the urine collection tube 3 is formed as an elongated tubular body where one end thereof is closed and the other end is opened. The urine collection tube 3 is made of a synthetic resin thermochromism material. A thermochromism material is, for example, a material that reversibly changes between a color developing (colored) state and a non-color developing (non-colored) state. Examples of the color developing state include a pink color, a red color, an orange color, a blue color, a green color, and a black color. An example of the non-color developing state includes a light white color.

Figure 9:
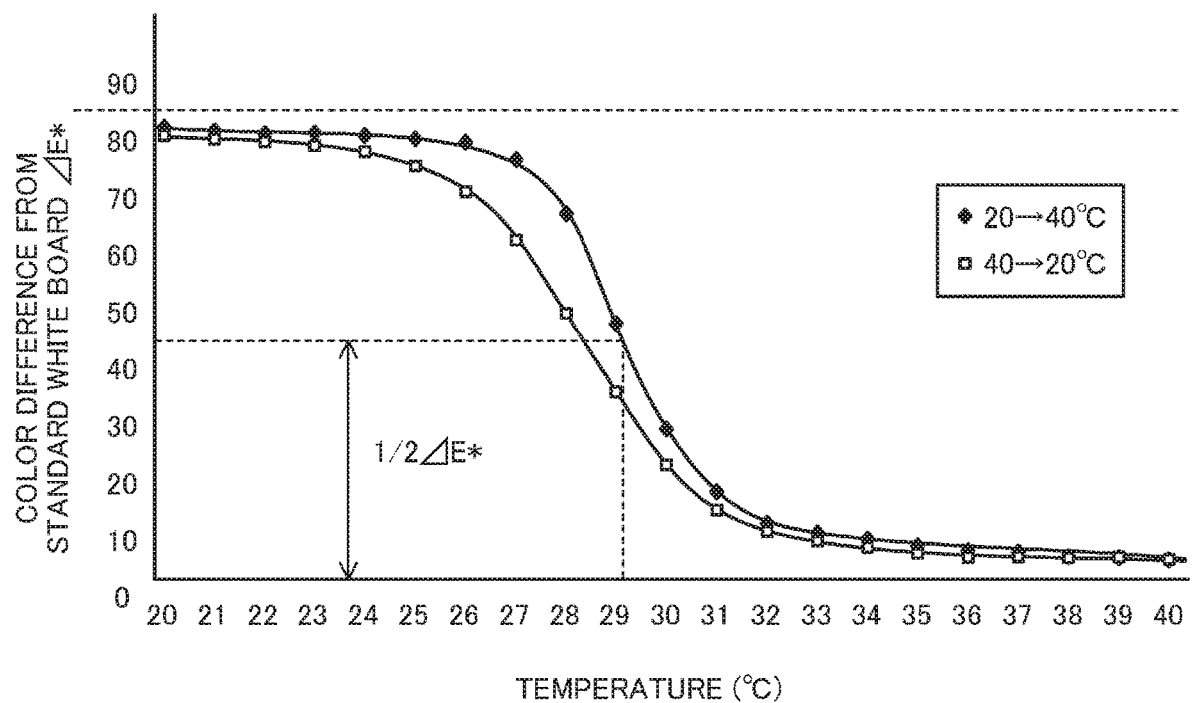
FIG. 9 is a graph showing a temperature change range of a thermochromism material.
Figure 10:
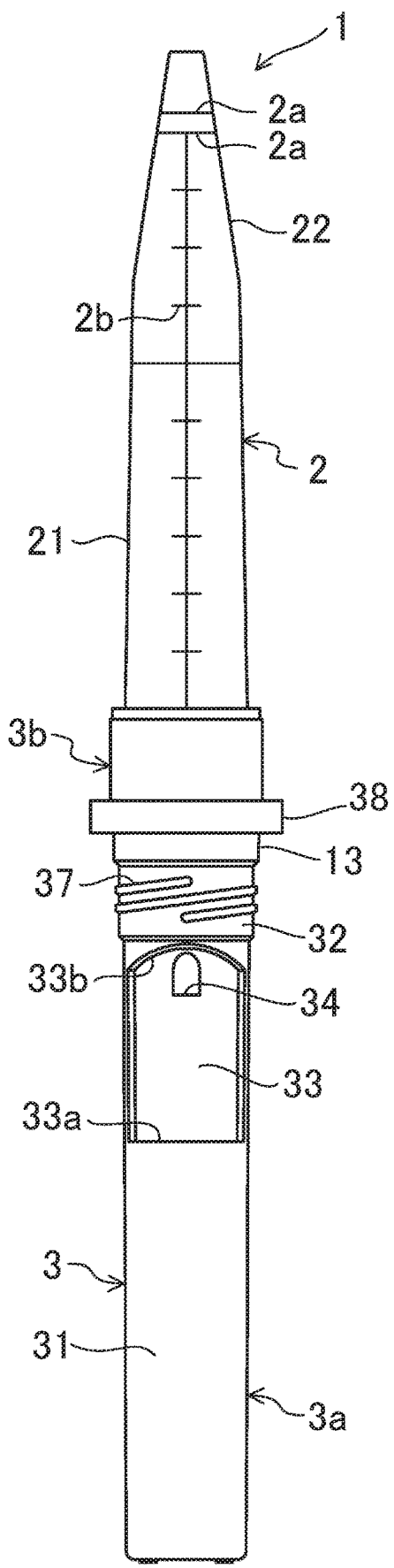
FIG. 10 is a front view of the urine sampling container without the cover tube according to the second embodiment of the present invention.
Figure 11:
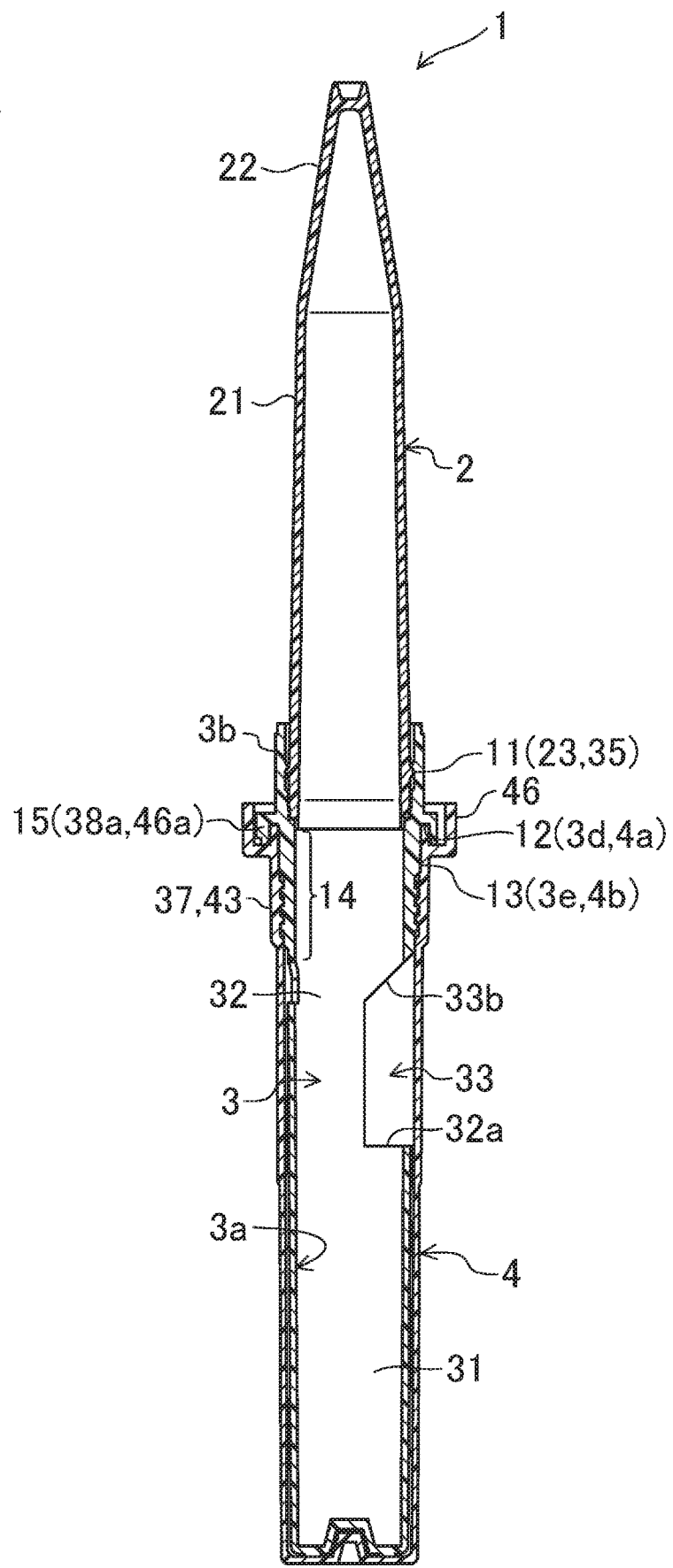
FIG. 11 is a longitudinal sectional view of the urine sampling container with the cover tube.
Figure 12:
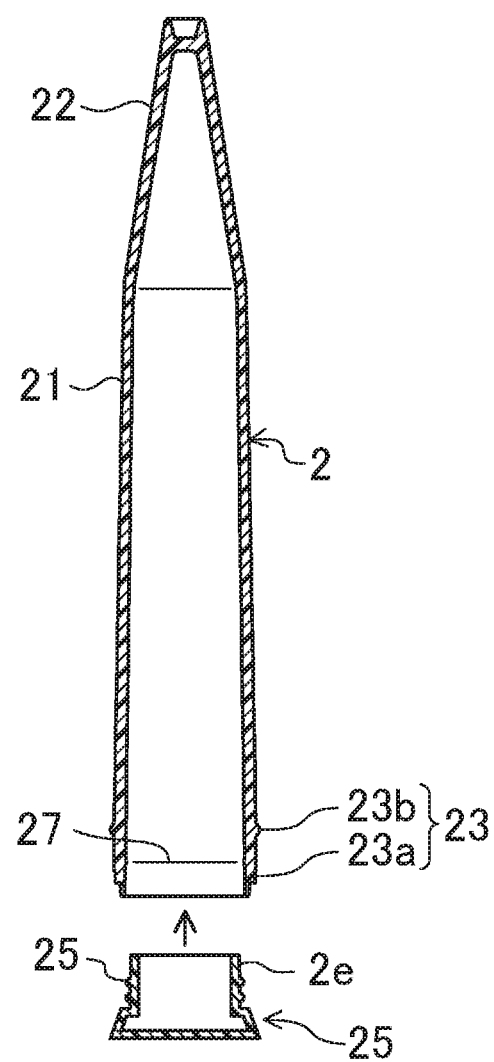
FIG. 12 is a longitudinal sectional view of the storage tube.

The discoloration temperature range of the thermochromism material can be selected within the range of, for example, −5° C. to +55° C. in an appropriate manner. In this embodiment, as illustrated in FIG. 9, when the temperature approaches a first temperature close to a human body temperature (approximately 35° C.), the state turns to the non-color developing state. When the temperature approaches a second temperature (approximately 25° C.) lower than the first temperature, the state turns to the color developing state. Note that in FIG. 9, the mark "♦" represents discoloration appearing when the temperature increases from 20° C. to 40° C. The mark "☐" represents discoloration appearing when the temperature decreases from 40° C. to 20° C.

As described above, the urine collection tube 3 is made of a discoloration material that is in a colored state at an ordinary temperature (the second temperature) and changes to a non-color developing state when the temperature increase from the second temperature to the first temperature due to the temperature of the collected urine. Note that, in contrast, the urine collection tube 3 may be made of a discoloration material that is in a non-coloring state at the second temperature and changes from the non-coloring state to a coloring state when the temperature changes from the second temperature to the first temperature.

The thermochromism material can be, for example, a transparent synthetic resin kneaded with a thermochromism ink powder (microcapsule). This thermochromism ink powder does not contain harmful substances such as heavy metals (arsenic, lead, cadmium, mercury, selenium, antimony, chromium, barium, etc.).

The urine collection tube 3 includes a main body 3a and a large diameter section 3b formed at the opening end. The main body 3a includes a measurement section 31, occupying substantially a half of the entirety, in the lower half of FIG. 4, and a urine collection section 32, occupying substantially a half of the entirety, in the upper half of FIG. 4. The measurement section 31 includes one end blocked, and measures urine necessary for the urinalysis. For example, the measurement section 31 of the urine collection tube 3 has a storage volume of 10 ml (milliliter). Note that the storage volume of the measurement section 31 may be 15 ml (milliliter) or 20 ml (milliliter). In short, the storage volume of the measurement section 31 may be 10 ml (milliliter) or more depending on a requirement for inspection or the like. Conversely, the storage volume of the measurement section 31 may be less than 10 ml (milliliter).

The urine collection section 32 of the urine collection tube 3 is formed as a tubular body where one end is continuous with the measurement section 31 and the other end is opened. The urine collection section 32 includes a urine collection port 33 and an auxiliary port 34. The urine collection port 33 is an opening into which the urine is injected at the time of collecting the urine, and penetrates from the outer peripheral surface to the inner peripheral surface of the urine collection tube 3. The urine collection port 33 is formed by cutting out an over-half part of the urine collection tube 3 in the circumferential direction.

One end of the urine collecting port 33 closer to the measurement section 31 is formed on an orthogonal surface 33a that coincides with the radial direction of the urine collection tube 3, and the other end is formed on an inclined surface 33b that is inclined toward the opening end. Then, the measurement section 31 is from the orthogonal surface 33a of the urine collection port 33 to the closed end of the urine collection tube 3.

The auxiliary port 34 penetrates from the outer peripheral surface opposite to the urine collection port 33 to the inner peripheral surface of the urine collection tube 3. Note the number of the auxiliary ports 34 may be two or more. The auxiliary port 34 is formed to operate an air ventilation at the time of urine collection to facilitate the urine collection, and to prevent deformation at the time of molding.

The large diameter section 3b is continuous with the opening end of the urine collection section 32, and is larger than the outer diameter of the urine collection section 32, such that the opening end of the storage tube 2 is freely inserted thereto.

Figure 6:
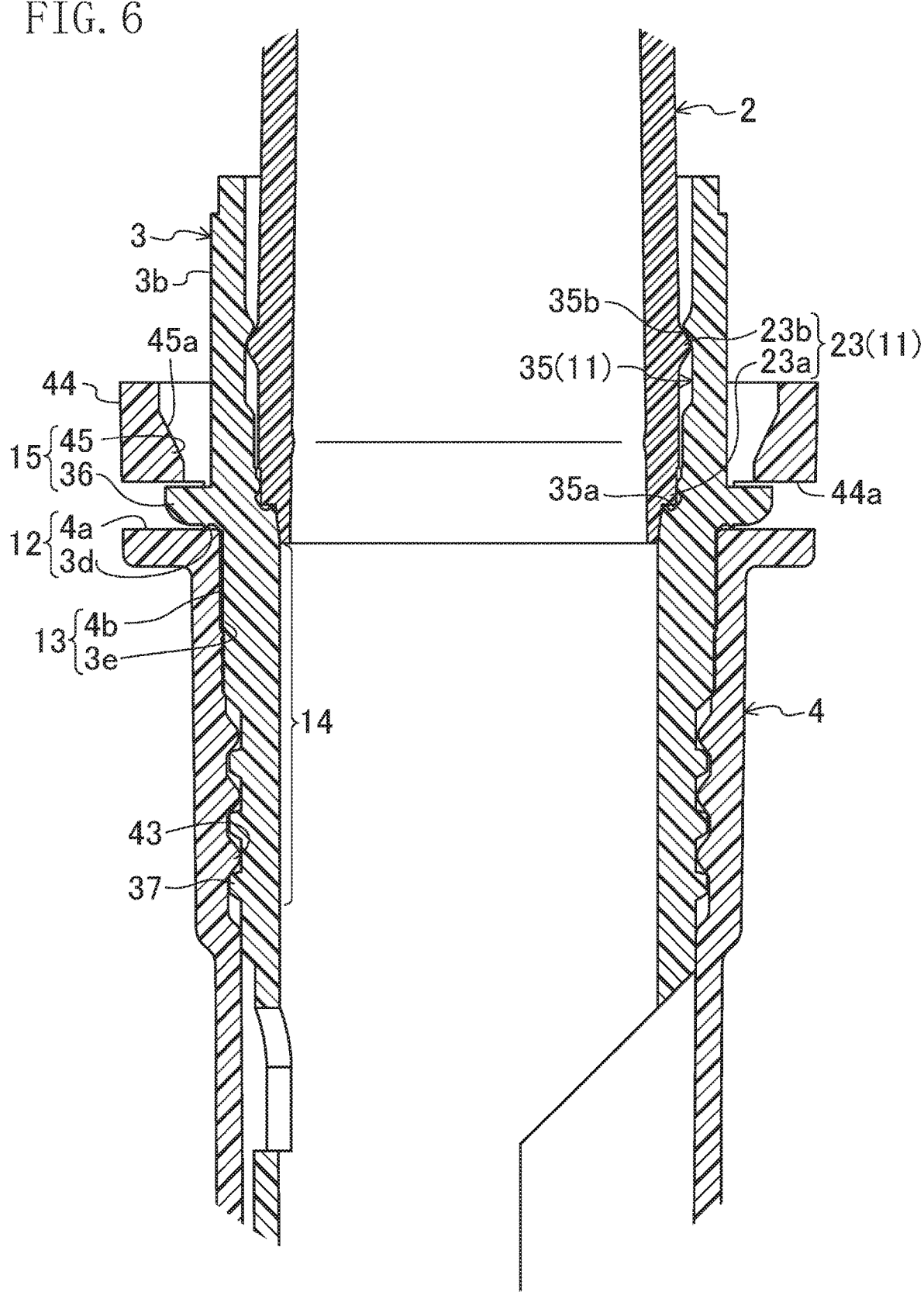
FIG. 6 is an enlarged sectional view of a main part of the urine sampling container.
Figure 7:
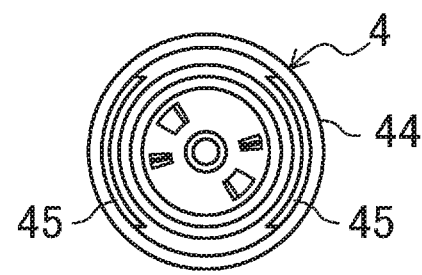
FIG. 7 is a plan view of the cover tube.
Figure 8:
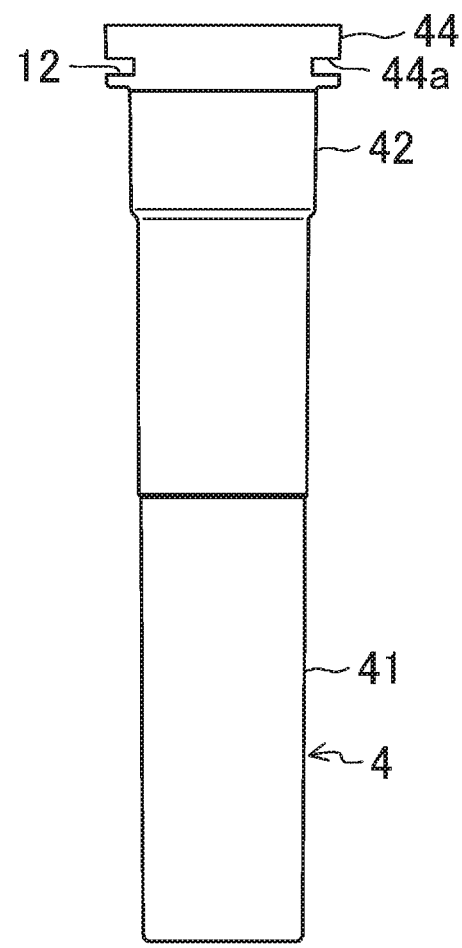
FIG. 8 is a front view of the cover tube.

As illustrated in FIG. 6 which is an enlarged sectional view of a main part of the urine sampling container 1, the large diameter section 3b has the inner peripheral surface provided with a circumferential groove 35 engaged with the first circumferential raised section 23a and the second circumferential raised section 23b of the circumferential raised section 23 of the storage tube 2. The circumferential groove 35 includes a first shoulder 35a abutting and engaging with the first circumferential raised section 23a, located on the open end side of the storage tube 2, from the open end side of the storage tube 2; and a second shoulder 35b abutting and engaging with the second circumferential raised section 23b, located closer to the closed end side of the storage tube 2 than the first circumferential raised section 23a, from the closed end side of the storage tube 2, and constitutes the holding mechanism 11 together with the circumferential raised section 23. The holding mechanism 11 is formed at a position displaced from a joint section 14 at which the urine collection tube 3 and the cover tube 4 overlap to be integrated together.

The circumferential raised section 23 of the storage tube 2 and the circumferential groove 35 of the urine collection tube 3 make the storage tube 2 and the urine collection tube 3 attachable and detachable. The circumferential raised section 23 of the storage tube 2 and the circumferential groove 35 of the urine collection tube 3 enables insertion and removal between the storage tube 2 and the urine collection tube 3 without a relative rotation to allow the storage tube 2 and the urine collection tube 3 to be attachable and detachable.

An end surface of the large diameter section 3b closer the urine collection section 32 is formed as a step surface 3d next to the main body 3a, and the step surface 3d is formed in an orthogonal plane coincident with the radial direction of the urine collection tube 3. The large diameter section 3b has an outer peripheral end portion integrated with a flange section 36 constituting a retaining mechanism 15. The flange section 36 is formed so as to be inserted into the end portion of the cover tube 4, and the flange section 36 includes a lower surface, which is the step surface 3d.

A fixing screw 37 fixing the cover tube 4 is formed between the opening end and the urine collection port 33 which is a part of the outer peripheral surface of the main body 3a of the urine collection tube 3. The fixing screw 37 is configured so that the cover tube 4 is mounted in a state in which the urine collection tube 3 is inserted into the cover tube 4.

Figure 5:
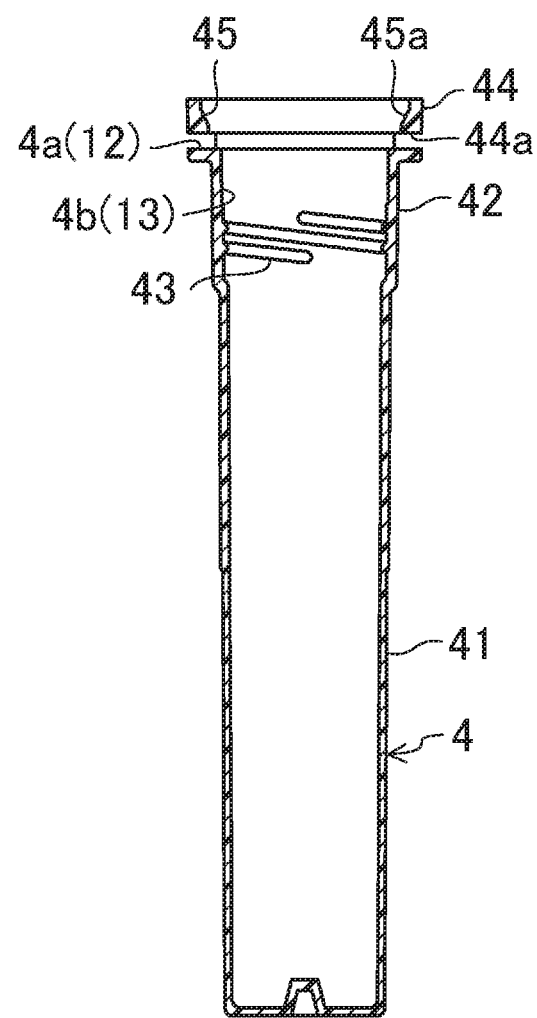
FIG. 5 is a longitudinal sectional view of the cover tube.

As illustrated in FIG. 5, the cover tube 4 is formed as an elongated tubular body where one end thereof is closed and the other end is opened. The cover tube 4 is formed from a colored material such as a synthetic resin. Note that the material of the cover tube 4 is not limited to a colored material, and may be formed from other various materials.

The cover tube 4 is formed slightly larger in diameter than the urine collection tube 3 so as to enable collection tube 3 to engage therewith and be inserted and removed therefrom.

The cover tube 4 has a length that allows the entirety of the body portion 3a of the urine collection tube 3 to be inserted thereto when the urine collecting port 33 is closed. The cover tube 4 includes a main body 41 closed at one end and opened at the other end and closing the urine collecting port 33 and a large diameter section 42 formed at the opening end of the main body 41. The large diameter section 42 is formed so as to be engaged with the urine collection tube 3 at the joint section 14. On the inner peripheral surface of the large diameter section 42, a fixing screw 43 screwed into the fixing screw 37 of the urine collection tube 3 is formed.

Between the urine collection tube 3 and the cover tube 4, provided are the retaining mechanism 15, an end surface sealing unit 12 and a side surface sealing unit 13.

The retaining mechanism 15 is provided near the opening ends of the urine collection tube 3 and the cover tube 4 to prevent the cover tube 4 from being disengaged from the urine collection tube 3 in a state in which the urine collection tube 3 is inserted into and fitted with the cover tube 4. The retaining mechanism 15 includes the flange section 36 formed on the entire periphery of the outer peripheral surface of the urine collection tube 3, and a stopper tube 44 formed on the cover tube 4 allowing an insertion of the flange section 36 of the urine collection tube 3. On the inner peripheral surface of the stopper tube 44, a stopper protrusion (undercut section) 45 protruding inward in the radial direction so as to be engaged with the flange section 36 is formed at each two positions opposed to each other. The inner peripheral surface of the stopper protrusion 45 is formed as an inclined surface 45a of which the amount of protrusion increases from the opening end of the stopper tube 44 toward the back thereof. Further, the stopper tube 44 has a slit 44a positioned radially outward of the flange section 36, and the flange section 36 is positioned within the slit 44a.

In the retaining mechanism 15, as the cover tube 4 of the imaginary line in FIG. 1 is fastened to the urine collection tube 3 with the fixing screws 37, 43, the flange section 36 moves into the stopper tube 44. When the flange 36 passes over and engages with the stopper protrusion 45, the cover tube 4 is not removed from the urine collection tube 3 even if the cover tube 4 is turned in the reverse direction.

The end surface sealing unit 12 seals a portion between the opening of the cover tube 4 and the urine collection tube 3, and includes an end surface 4a on the lower side of the slit of the cover tube 4 and an end surface 3d of the flange section 36 of the urine collection tube 3. That is, as illustrated in FIG. 6, the end surface sealing unit 12 is configured so that, when the cover tube 4 is fastened to the urine collection tube 3, the end surface 4a of the slit of the cover tube 4 comes into close contact with the end surface 3d of the flange section of the urine collection tube 3.

The side surface sealing unit 13 seals a portion between the opening end of the cover tube 4 and the opening end of the urine collection tube 3 at the side surface, and includes a sliding surface 4b formed on the cover tube 4, and a sliding surface 3e formed on the urine collection tube 3. The sliding surface 4b of the cover tube 4 is a part of the inner peripheral surface of the main body 41 of the cover tube 4, and is formed at the peripheral edge of the opening end. The sliding surface 3e of the urine collection tube 3 is a part of the outer peripheral surface of the main body 3a in the urine collection tube 3, and is formed between the opening end and the fixing screw 37. As illustrated in FIG. 6, the sliding surface 4b of the cover tube 4 and the sliding surface 3e of the urine collection tube 3 are configured to be in close contact with each other when the urine collection tube 3 is inserted into the cover tube 4. The portion at which the cover tube 4 and the urine collection tube 3 overlap one another and the portion including the fixing screws 37, 43 constitute the joint section 14.

The storage tube 2 includes a fixing raised section 27 for fixing the cap 25. The fixing raised section 27 is annularly formed on the inner peripheral surface of the opening end of the main body 21 of the storage tube 2. On the other hand, the cap 25 includes a fitting section 2e to be fitted into the main body 21 of the storage tube 2, and a ring-shaped raised section 2f is formed on the outer peripheral face of the fitting section 2e. When the cap 25 is fitted into the storage tube 2, and the raised section 2f of the cap 25 passes over the fixing raised section 27, the fixing raised section 27 generates a "clink" sound that indicates a completion of the fitting.

Procedure for Using Urine Sampling Container

Next, a procedure for using the urine sampling container 1 will be described.

First, in an unused state before urine collection, the urine sampling container 1 is placed in a packaging bag. At this time, the opening end of the storage tube 2 is inserted into the opening end of the urine collection tube 3 so that the storage tube 2 and the urine collection tube 3 are coupled together. In addition, as shown by the imaginary lines in FIG. 1, the urine collection tube 3 is merely lightly inserted into the cover tube 4 so that the cover tube 4 is easily disengaged from the urine collection tube 3.

Next, at the time of urine collection, the examinee takes out the urine sampling container 1 from the packaging bag, and removes the cover tube 4 from the urine collection tube 3. The urine collection tube 3 is lightly inserted in the cover tube 4, and thus the cover tube 4 is easily removed from the urine collection tube 3. Then, in a state in which the urine collection tube 3 is attached to the storage tube 2, the examinee grips the storage tube 2 with the urine collection tube 3 oriented downward. Next, when the examinee applies urine to the urine collection port 33, the urine flows from the urine collection port 33 into the urine collection tube 3, and accumulates in the measurement section 31. Then, the collection of urine is completed. When a predetermined amount (for example, 10 ml) of urine is injected into the measurement section 31 in this urine collection, the urine leaks from the urine collection port 33 to the outside of the urine collection tube 3. Thus, an necessary amount for urinalysis is reliably collected, and no redundant urine is collected. At the time of urine collection, the difference in the wall thickness between the storage tube 2 and the urine collection tube 3 is small, and the difference in the rigidity therebetween is also small, such that the storage tube 2 and the urine collection tube 3 are not easily separated.

Upon completion of this urine collection, the urine sampling container 1 is transferred to an laboratory or the like.

During the transportation, as illustrated in FIG. 2, the urine collection tube 3 oriented downward is inserted into the cover tube 4 so that the urine collection tube 3, which is a dirty part, is covered. At this time, when the urine collection tube 3 is inserted into the cover tube 4, the urine collection port 33 is closed by the cover tube 4. Next, the urine collection tube 3 is turned with respect to the cover tube 4 to tighten the fixing screws 37, 43 to allow the flange section 36 to pass over and engage with the stopper protrusion 45. At this time, the fixing screws 37, 43 join and fix the cover tube 4 and the urine collection tube 3, and, as illustrated in FIGS. 2 and 6, the flange section 36 and the stopper protrusion 45 prevent the fixing screws 37, 43 from turning in the reverse direction. Thus, the cover tube 4 and the urine collection tube 3 cannot be disengaged from each other even if the cover tube is turned in the reverse direction.

When the cover tube 4 and the urine collection tube 3 are joined together as illustrated in FIGS. 2 and 6, the opening end surface 4a of the cover tube 4 comes into close contact with the step surface 3d of the large diameter section 3b of the urine collection tube 3, and the portion between the cover tube 4 and the urine collection tube 3 is sealed (the end surface sealing unit 12). Further, when the urine collection tube 3 is inserted into the cover tube 4, the sliding surface 4b of the cover tube 4 and the sliding surface 3e of the urine collection tube 3 come into close contact with each other, and the portion between the cover tube 4 and the urine collection tube 3 is sealed (the side surface sealing unit 13). Thus, the leakage of urine is prevented.

Next, the urine sampling container 1 inverted upside down is transferred to the laboratory or the like while the storage tube 2 oriented downward is inserted in the container stand or the like. At this time, when the urine collection tube 3 is turned upside down, the urine flows into the storage tube 2, and the urine is stored in the storage tube 2.

Then, in the laboratory or the like, when the examiner bends the storage tube 2 in an "L" shape at the joint section with respect to the urine collection tube 3 and the cover tube 4 integrated together, the holding mechanism 11 is disengaged. Unlike the time of urine collection, the rigidity of the urine collection tube 3 and the cover tube 4 integrated together is larger than that of the storage tube 2, and the storage tube 2 is easily deformed. Thus, the storage tube 2 is disengaged from the urine collection tube 3 and the cover tube 4. Then, only the storage tube 2 storing the urine is set in the examination device.

This embodiment may be as follows. After urine collection is finished, the urine collection tube 3 oriented downward may be inserted into the cover tube 4. Then, after the urine collection port 33 is closed by the cover tube 4, the urine sampling container 1 is inverted upside down, and then the urine is stored in the storage tube 2. Further, after the storage tube 2 is removed from the urine collection tube 3 and the cover tube 4, the cap 25 is fitted into the opening end of the storage tube 2. Then, the storage tube 2 is transferred to the laboratory or the like and set in the examination device.

In the urinalysis, the storage tube 2 is installed in a centrifugal separator, and a liquid component and a solid component are separated. Then, decantation is performed to discard the liquid component of a supernatant. Then, the storage tube 2 is inverted to remove the liquid component, and a precipitate remaining in the storage tube is used for an examination.

In this embodiment, at the time of urine collection, the cover tube 4 is not attached on the urine sampling container 1, and the storage tube 2 and the urine collection tube 3 are joined by the holding mechanism 11 including the circumferential raised section 23 and the circumferential groove 35. At this time, the difference in the wall thickness between the storage tube 2 and the urine collection tube 3 is small (or there is no difference in the wall thickness), and thus the difference in the rigidity between the storage tube 2 and the urine collection tube 3 is small, such that the portion coupled by the holding mechanism 11 is less likely to be deformed. On the other hand, when the cover tube 4 is attached to the urine collection tube 3 after the urine collection, the urine collection tube 3 and the cover tube 4 overlap and are integrated with each other through the fixing screws 37, 43 so that the wall thickness of the joint section 14 is larger than that of the storage tube 2. Thus, the rigidity of the urine collection tube 3 and the cover tube 4 integrated together is larger than that of the storage tube 2, and the storage tube 2 is easily deformed at the portion coupled by the holding mechanism 11.

Advantages of First Embodiment

According to this embodiment, at the time of urine collection, the difference in the rigidity between the storage tube 2 and the urine collection tube 3 is small, and the coupling portion between the storage tube 2 and the urine collection tube 3 is less likely to be deformed. Thus, the storage tube 2 and the urine collection tube 3 are reliably joined and not easily disengaged. On the other hand, at the time of examination, the rigidity of the urine collection tube 3 and the cover tube 4 integrated together is larger than that of the storage tube 2, and the storage tube 2 is easily deformed at the coupling portion. Thus, the examiner can easily bend and disengage the storage tube 2 into the "L" shape at the coupling portion with respect to the urine collection tube 3 and the cover tube 4 integrated together. As such, this embodiment provides the structure in which the urine collection tube and the storage tube are securely coupled at the time of urine collection, and the storage tube is easily disengaged from the urine collection tube at the time of examination.

According to this embodiment, the cover tube 4 is not removed from the urine collection tube 3 only by inserting the flange section 36 into the stopper tube 44 and engaging the flange section 36 with the stopper protrusion 45. Thus, the retaining mechanism 15 having a simple configuration can be achieved.

According to this embodiment, when the circumferential raised section 23 formed on the outer peripheral surface of the storage tube 2 and the circumferential recessed section 35 formed on the inner peripheral surface of the urine collection tube 3 are fitted with each other, the first shoulder 35a comes into contact with the first circumferential raised section 23a from the opening end of the storage tube 2, and the second shoulder 35b comes into contact with the second circumferential raised section 23b from the closed end of the storage tube 2, so that the storage tube 2 is kept inserted in the urine collection tube 3. Thus, the holding mechanism including the circumferential raised section 23 and the circumferential recessed section 35 can be achieved with a simple configuration. In addition, the set of the first circumferential raised section 23a and the first shoulder 35a is located closer to the opening end of the storage tube 2, and the set of the second circumferential raised section 23b and the second shoulder 35b is located closer to the closed end of the storage tube 2 so that these set are located apart from each other. Thus, the storage tube 2 is inserted in and stably held in the urine collection tube 3.

According to this embodiment, when urine is applied to the urine collection tube 3 at the time of urine collection, the urine collection tube 3 having had a low temperature (a room temperature) is discolored due to the influence of a urine temperature (approximately a body temperature). In some conventional cases, it was difficult to determine a completion of urine collection in an environment such as dark surroundings. In contrast, in this embodiment, the urine collection tube 3 is discolored so that the examinee can surely recognize a completion of urine collection.

Second Embodiment of the Invention

The second embodiment of the present invention illustrated in FIGS. 10 to 18 will be described.

The second embodiment of the present invention is different from the first embodiment in the configuration of the retaining mechanism 15.

Figure 13:
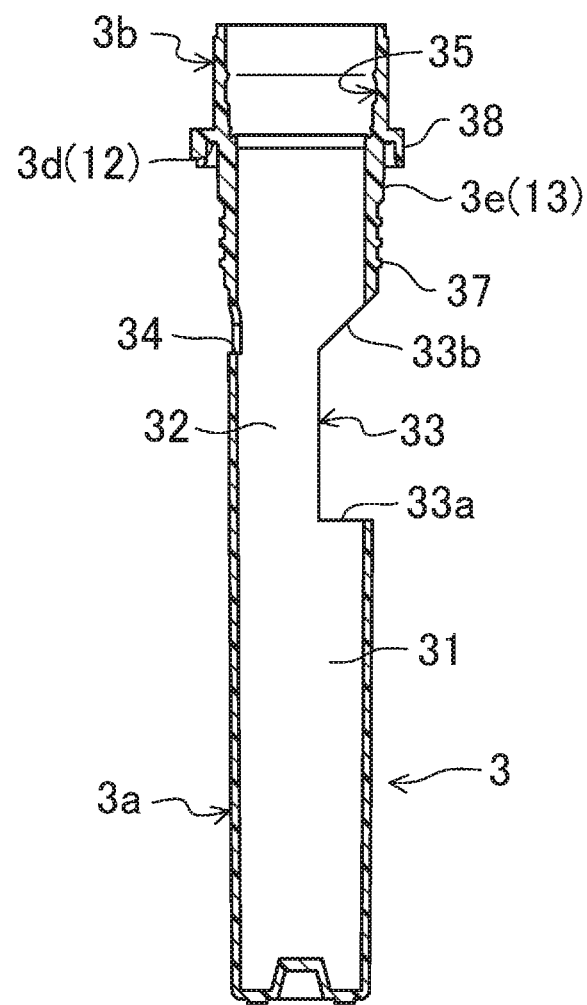
FIG. 13 is a longitudinal sectional view of the urine collection tube.
Figure 14:
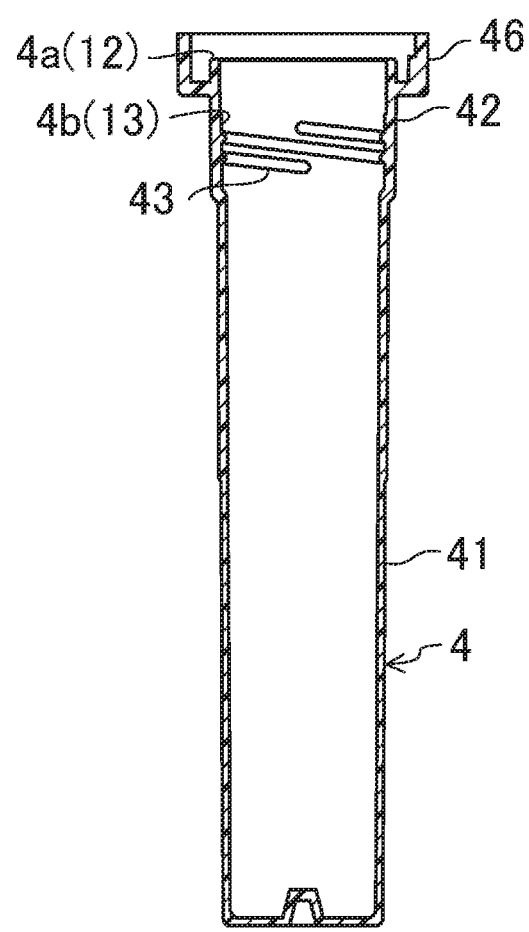
FIG. 14 is a longitudinal sectional view of the cover tube.
Figure 15:
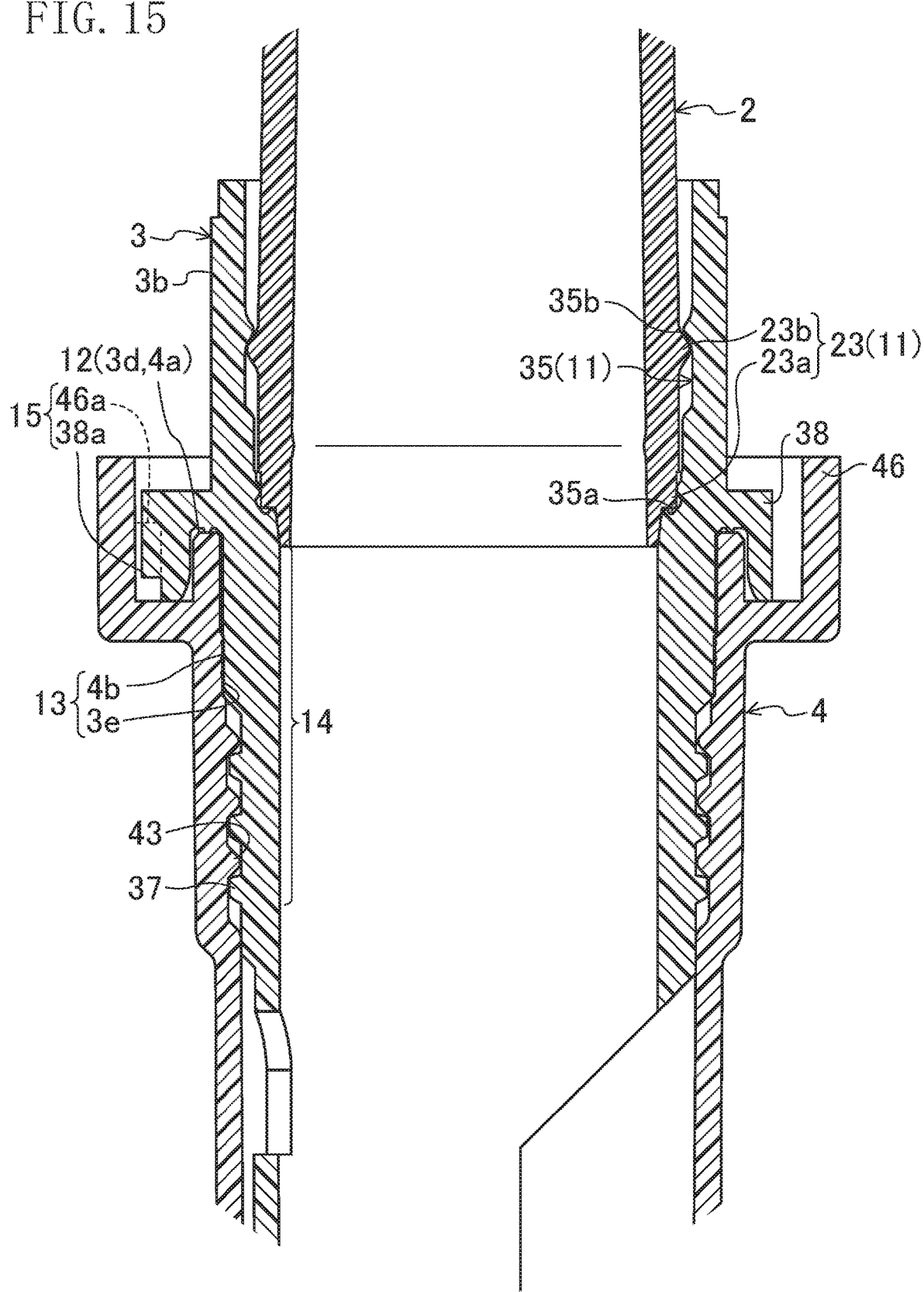
FIG. 15 is an enlarged sectional view of a main part of the urine sampling container.
Figure 16:
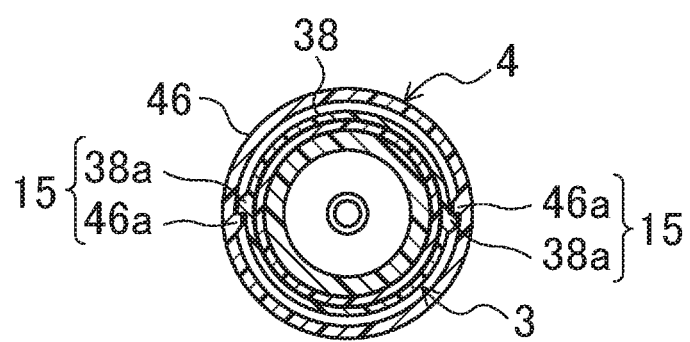
FIG. 16 is a plan view of the cover tube.
Figure 17:
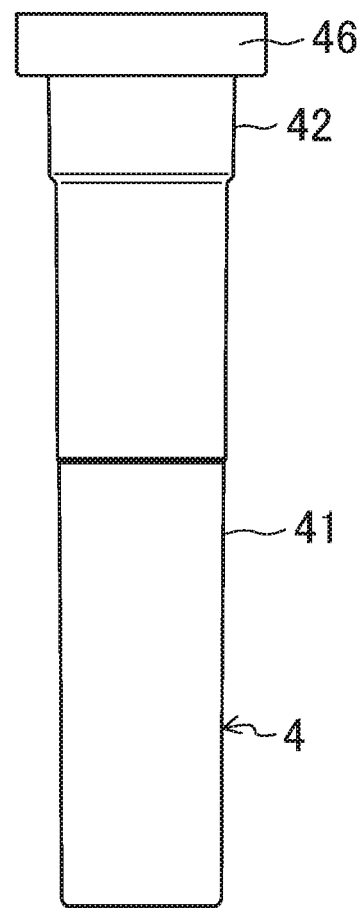
FIG. 17 is a front view of the cover tube.
Figure 18:
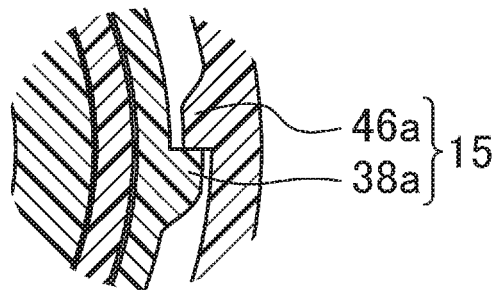
FIG. 18 is a partially enlarged view of FIG. 16.

In this embodiment, as illustrated in FIGS. 13 to 15, a first anti-rotation ring 38 is formed at the position of the step surface 3d in the large diameter section 3b of the urine collection tube 3, and a second anti-rotation ring 46 is formed on the large diameter section 42 of the cover tube 4. The first anti-rotation ring 38 and the second anti-rotation ring 46 are formed to engage with each other.

As illustrated in FIGS. 15 to 18, a first stopper raised section 38a is formed on the outer peripheral surface of the first anti-rotation ring 38 of the urine collection tube 3, and a second stopper raised section 46a is formed on the inner peripheral surface of the second anti-rotation ring 46 of the cover tube 4. The first stopper raised section 38a and the second stopper raised section 46a are engaged with each other in a state in which the urine collection tube 3 is screwed into the cover tube 4, and prohibit a rotation in the direction of loosening the fixing screws 37 and 43. The first stopper raised section 38a and the second stopper raised section 46a constitute the retaining mechanism 15.

As a precondition, the retaining mechanism 15 has the configuration in which the urine collection tube 3 is screwed into the cover tube 4 for joint. In this configuration, when the first stopper raised section 38a and the second stopper raised section 46a are engaged with each other as illustrated in FIG. 15, the cover tube 4 is not removed from the urine collection tube 3 even if the cover tube 4 is turned in the reverse direction.

The end surface sealing unit 12 includes the opening end surface 4a of the cover tube 4 and the step surface 3d of the urine collection tube 3 to seal the portion between the opening end of the cover tube 4 and the urine collection tube 3. The configuration is substantially the same as that of the first embodiment. That is, as illustrated in the enlarged view of FIG. 15, the end surface sealing unit 12 is formed such that, when the cover tube 4 is screwed into the urine collection tube 3, the opening end surface 4a of the large diameter section 42 of the cover tube 4 comes into close contact with the step surface 3d of the diameter section 3b.

The other configurations are the same as those in the first embodiment.

Also in this embodiment, at the time of urine collection, the difference in the rigidity between the storage tube 2 and the urine collection tube 3 is small, and the coupling portion between the storage tube 2 and the urine collection tube 3 is less likely to be deformed. Thus, the storage tube 2 and the urine collection tube 3 are reliably joined and not easily disengaged. On the other hand, at the time of examination, the rigidity of the urine collection tube 3 and the cover tube 4 integrated together is larger than that of the storage tube 2, and the storage tube 2 is easily deformed at the coupling portion. Thus, the examiner can easily bend and disengage the storage tube 2 into the "L" shape at the coupling portion with respect to the urine collection tube 3 and the cover tube 4 integrated together. As such, this embodiment provides the structure in which the urine collection tube and the storage tube are securely coupled at the time of urine collection, and the storage tube is easily disengaged from the urine collection tube at the time of examination.

According to this embodiment, when the urine collection tube 3 is screwed to the cover tube 4, the first stopper raised section 38a and the second stopper raised section 46a are engaged and prohibited from turning in the reverse direction, and the storage tube 2 is not removed from the urine collection tube 3. Thus, the retaining mechanism 15 can be achieved with a simple structure.

The other same advantages as those of the first embodiment can be achieved.

Other Embodiments

The above embodiments may be configured as follows.

In the above embodiments, the urine collection tube 3 is made of a discoloration material, but in the present invention, the urine collection tube 3 does not necessarily have discoloration properties.

The retaining mechanism described in each of the above embodiments is an example of the configuration in which the cover tube 4 is not removed from the urine collection tube 3, but any other configurations may be adopted.

The holding mechanism 11 described in the above embodiments is not limited to the configuration in which the circumferential raised section 23 and the circumferential recessed section 35 are engaged with each other, and may adopt other configurations such as a screw connection. Still in that case, the rigidity is large when the urine collection tube 3 and the cover tube 4 are integrated together to increase, and thus the storage tube 2 can be easily removed.

In the present invention, as long as the retaining mechanism 15 is provided, the other specific configurations of the storage tube 2, the urine collection tube 3, and the cover tube 4 are not limited to those of the above embodiment, and can be changed if necessary.

Note that the above embodiments are essentially preferred examples, and not intended to limit the scope application, or usage of the present invention.

INDUSTRIAL APPLICABILITY

As described above, the present invention is useful for a urine sampling container for urinalysis.

DESCRIPTION OF REFERENCE CHARACTERS

1 Urine Sampling Container
2 Storage Tube
3 Urine Collection Tube
4 Cover
11 Holding Mechanism
15 Retaining Mechanism
23 Circumferential Raised Section
23a First Circumferential Raised Section
23b Second Circumferential Raised Section
33 Urine Collection Port
35 Circumferential Recessed Section
35a First Shoulder
35b Second Shoulder
36 Flange Section
38a First Stopper Raised Section
44 Stopper Tube
44a Slit
45 Stopper Protrusion
45a Inclined Surface
46a Second Stopper Raised Section

The invention claimed is:

1. A urine sampling container, comprising:
a storage tube formed as an elongated tube and storing urine, where one end of the storage tube is a closed end and the other end of the storage tube is an opening end;
a urine collection tube formed as an elongated tube and including a side surface having a urine collection port, where one end of the urine collection tube is a closed end and the other end of the urine collection tube is an opening end freely attachable to and detachable from the opening end of the storage tube;
a cover tube formed as an elongated tube, formed so that the urine collection tube can be inserted to and removed from the cover tube, and covering the urine collection port, where one end of the cover tube is a closed end and the other end of the cover tube is an opening end; and
an inner periphery of the urine collection tube and an outer periphery of the cover tube each include a fixing screw formed therein and configured to couple the urine collection tube and the cover tube,
in the inner periphery of the urine collection tube and the outer periphery of the cover tube, in addition to the fixing screws, a retaining mechanism formed near the opening ends of the urine collection tube and the cover tube to prevent the cover tube from being removed from the urine collection tube in a state in which the urine collection tube is inserted and fitted in the cover tube.

2. The urine sampling container of claim 1, wherein the retaining mechanism includes
a flange section formed on the urine collection tube and
a stopper tube formed on the cover tube allowing an insertion of the flange section of the urine collection tube, and
on an inner peripheral surface of the stopper tube, a stopper protrusion to be engaged with the flange section is formed.

3. The urine sampling container of claim 2, wherein an inner peripheral surface of the stopper protrusion is formed as an inclined surface of which the amount of protrusion increases from the opening end of the stopper tube toward the back thereof.

4. The urine sampling container of claim 3, wherein the stopper tube has a slit positioned radially outward of the flange section.

5. The urine sampling container of claim 1, wherein the retaining mechanism includes
a first stopper raised section formed on the urine collection tube and
a second stopper raised section formed on the cover tube, and
the first stopper raised section and the second stopper raised section are configured to prohibit a rotation in a direction of loosening a screw in a state in which the urine collection tube is screwed into the cover tube.

6. The urine sampling container of claim 1, wherein a holding mechanism for keeping the storage tube inserted in the urine collection tube is formed on an outer peripheral surface of the storage tube and an inner peripheral surface of the urine collection tube, at a position displaced from a joint section at which the urine collection tube and the cover tube overlap to be integrated together, and
the holding mechanism includes
a circumferential raised section formed on the outer peripheral surface of the storage tube and
a circumferential recessed section formed on the inner peripheral surface of the urine collection tube and fitted with the circumferential raised section.

7. The urine sampling container of claim 6, wherein the circumferential raised section of the holding mechanism includes
a first circumferential raised section located closer to the opening end of the storage tube and
a second circumferential raised section located closer to the closed end than the first circumferential raised section, and
the circumferential recessed section of the holding mechanism includes
a first shoulder coming into contact with the first circumferential raised section from the opening end of the storage tube and
a second shoulder coming into contact with the second circumferential raised section from the closed end of the storage tube.

8. The urine sampling container of claim 1, wherein the urine collection tube is made of a discoloration material exhibiting a respective different color at a first temperature corresponding to a human body temperature and at a second temperature lower than the first temperature.

9. The urine sampling container of claim 8, wherein the urine collection tube is made of a material that is in a non-coloring state at the second temperature and changes from the non-coloring state to a coloring state when the temperature changes from the second temperature to the first temperature.

10. The urine sampling container of claim 8, wherein the urine collection tube is made of a material that is in a coloring state at the second temperature and changes from the coloring state to a non-coloring state when the temperature changes from the second temperature to the first temperature.

* * * * *